United States Patent [19]

Kambin

[11] Patent Number: 5,545,228
[45] Date of Patent: Aug. 13, 1996

[54] OFFSET BONE BOLT

[75] Inventor: Parviz Kambin, Devon, Pa.

[73] Assignee: Smith & Nephew Richards Inc., Memphis, Tenn.

[21] Appl. No.: 16,681

[22] Filed: Feb. 11, 1993

Related U.S. Application Data

[63] Continuation-in-part of Ser. No. 965,346, Oct. 23, 1992, which is a continuation-in-part of Ser. No. 745,474, Aug. 15, 1991.

[51] Int. Cl.$^6$ ................ A61F 2/44; A61B 17/56
[52] U.S. Cl. ................ 623/17; 606/60; 606/61; 606/71; 606/73
[58] Field of Search .................. 606/60, 61, 71, 606/73; 623/13, 17; 433/174

[56] References Cited

U.S. PATENT DOCUMENTS

| | | |
|---|---|---|
| 4,653,481 | 3/1987 | Howland et al. . |
| 4,790,297 | 12/1988 | Luque . |
| 4,805,602 | 2/1989 | Puno et al. . |
| 4,887,596 | 12/1989 | Sherman . |
| 4,919,673 | 4/1990 | Willert et al. ............... 623/23 |
| 4,994,085 | 2/1991 | Sawai et al. ............... 623/23 |
| 5,024,213 | 6/1991 | Asher et al. . |
| 5,047,035 | 9/1991 | Mikhail et al. ............ 606/92 X |
| 5,062,850 | 11/1991 | MacMillan et al. ............ 623/17 |
| 5,129,899 | 7/1992 | Small et al. . |
| 5,129,900 | 7/1992 | Asher et al. . |
| 5,171,279 | 12/1992 | Mathews . |
| 5,176,679 | 1/1993 | Lin . |
| 5,192,283 | 3/1993 | Ling et al. ............... 606/92 X |
| 5,196,015 | 3/1993 | Neubardt . |
| 5,209,752 | 5/1993 | Ashman et al. ............ 606/61 |
| 5,234,431 | 8/1993 | Keller . |
| 5,242,443 | 9/1993 | Kambin . |
| 5,290,288 | 3/1994 | Vignaud et al. ............ 606/73 X |
| 5,300,073 | 4/1994 | Ray et al. ............... 606/61 |
| 5,306,275 | 4/1994 | Bryan ............... 606/73 X |
| 5,312,404 | 5/1994 | Asher et al. ............ 606/73 X |
| 5,344,422 | 9/1994 | Frigg ............... 606/60 |
| 5,415,659 | 5/1995 | Lee et al. ............... 606/61 |

FOREIGN PATENT DOCUMENTS

| | | |
|---|---|---|
| 0159007 | 4/1985 | European Pat. Off. . |
| 0468264A1 | 7/1991 | European Pat. Off. . |
| 0553424 | 8/1993 | European Pat. Off. ........ 606/61 |
| 3711091A1 | 4/1987 | Germany . |
| 9314721 | 8/1993 | WIPO ............... 623/17 |
| 4015554 | 7/1994 | WIPO ............... 623/17 |

*Primary Examiner*—David H. Willse
*Assistant Examiner*—Bruce E. Snow
*Attorney, Agent, or Firm*—Pravel, Hewitt, Kimball & Krieger

[57] ABSTRACT

A method for percutaneous fixation of a pair of vertebrae of a patient, which comprises posterolaterally entering the back of a patient percutaneously with a plurality of offset bone bolts, screwing each bone bolt into the medullary canal of the pedicles of adjacent thoracic and/or lumbar vertebrae or the pedicles of the L5 and S1 vertebrae, to a position where the proximal end thereof lies adjacent the fascia of the patient; inserting bone bolt linkages under the skin of the back of the patient and detachably securing the linkage means to the proximal ends of the bolts on the same side of the spinous processes of the vertebrae to restrict relative movement between the vertebrae. A kit is provided for percutaneous fixation of vertebrae of a patient, comprising a plurality of offset bone bolts of different sizes, yet of a size to enable the distal end of each bolt to be screwed into the medullary canal of a pedicle of a vertebra with the proximal end thereof lying adjacent the fascia of a patient.

7 Claims, 6 Drawing Sheets

FIG.1
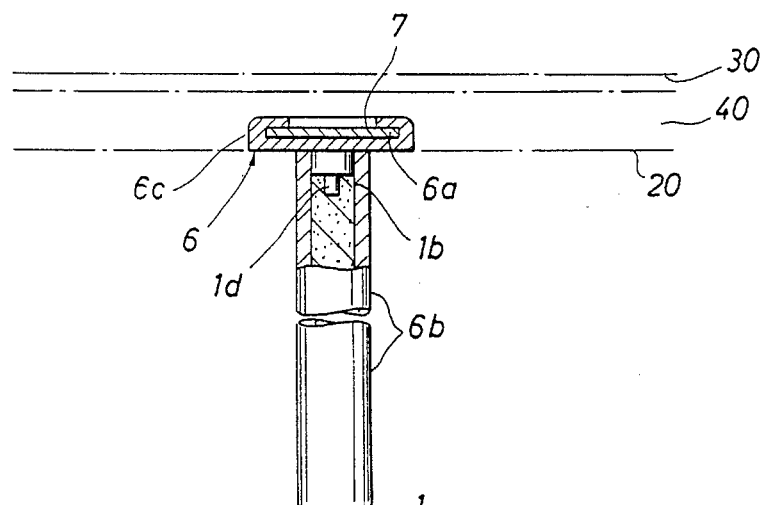
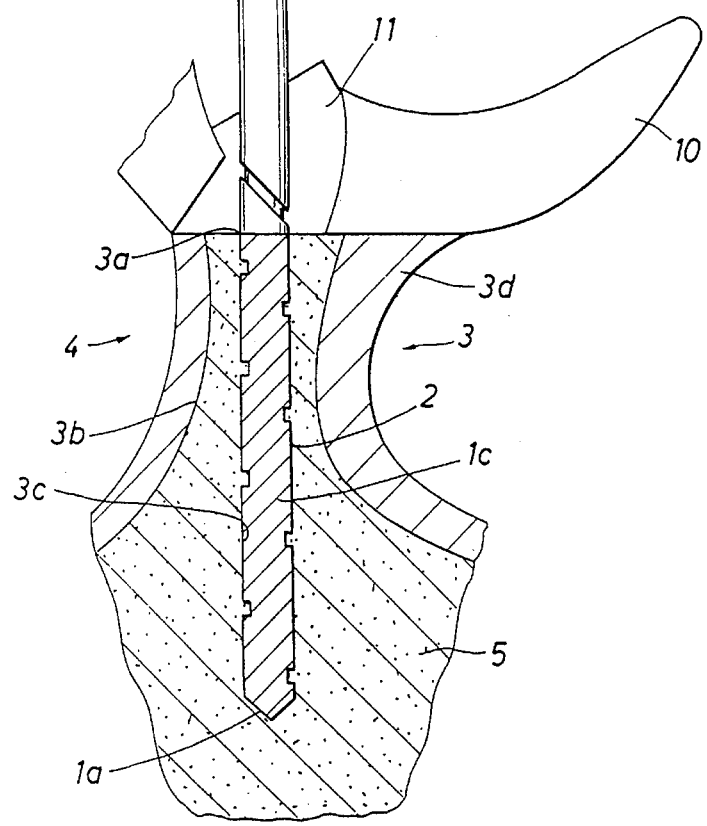
FIG.3
FIG.4
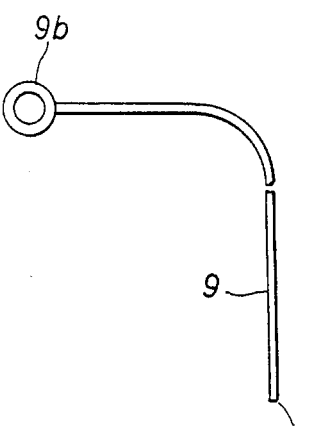

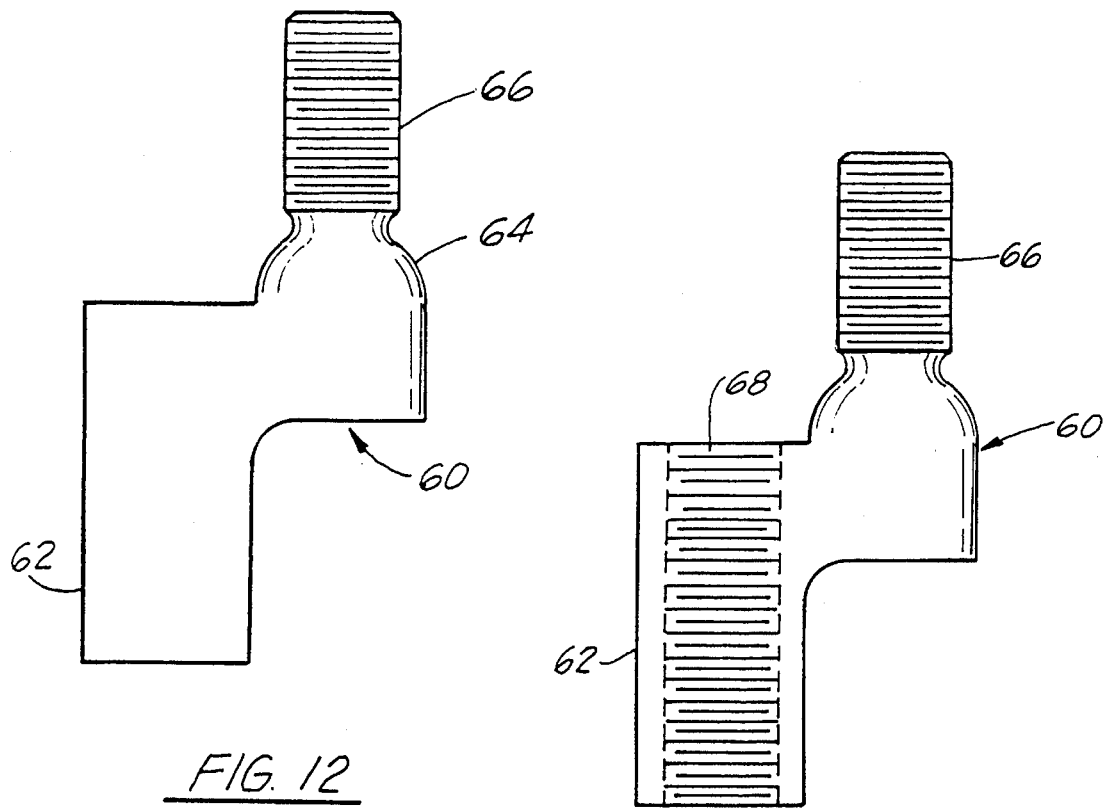
FIG. 12
FIG. 13
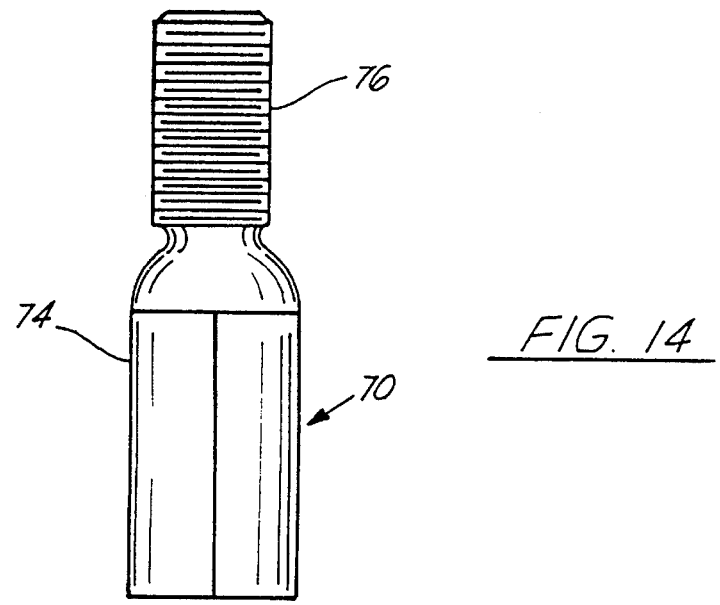
FIG. 14

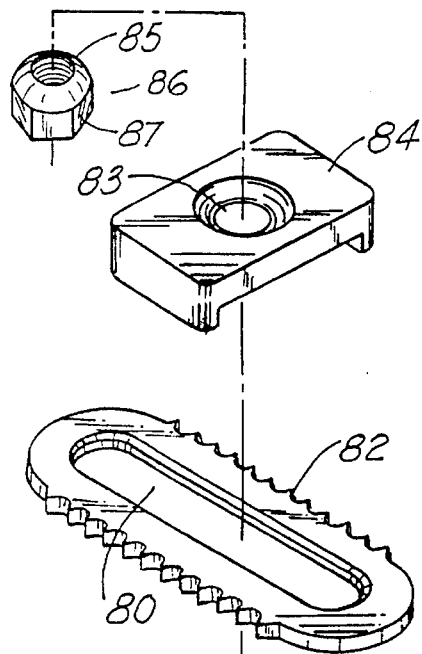
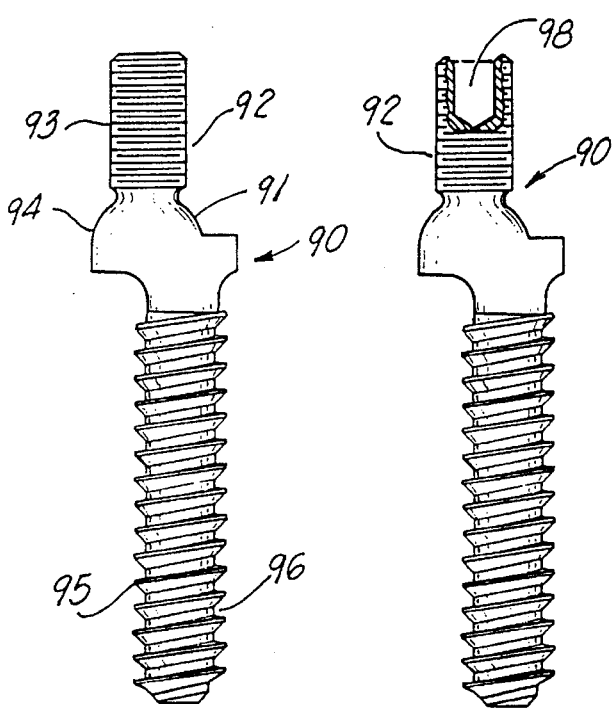
FIG. 17    FIG. 18
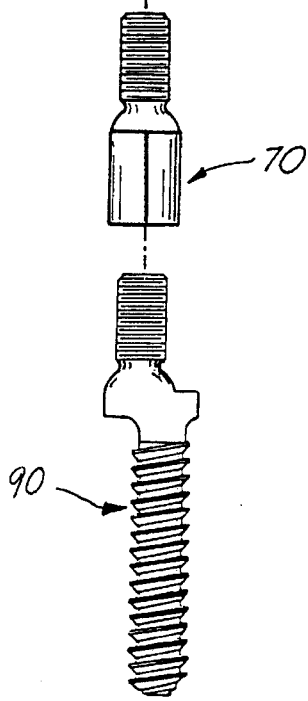
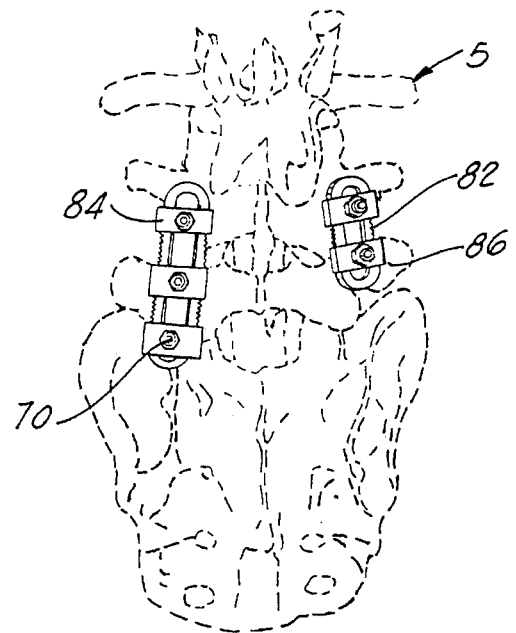
FIG. 19    FIG. 20

OFFSET BONE BOLT

FIELD OF THE INVENTION

This is a continuation-in-part of U.S. patent application Ser. No. 965,346 filed Oct. 23, 1992 which is a continuation-in-part of pending U.S. patent application Ser. No. 745,474 filed Aug. 15, 1991. The present invention relates to percutaneous interbody fusion with subcutaneous internal fixators. More particularly, the present invention relates to an internal fixator that allows for percutaneous fixation of lumbar vertebrae by means of a minimally invasive technique.

BACKGROUND OF THE INVENTION

The use of internal fixators for fixation of unstable fractures of the vertebrae is known. Also known is a system for internal fixation of vertebrae after the removal of one or more intervertebral discs. External fixation systems for the stabilization of thoracic and lumbar fractures have also been proposed.

The use of existing internal fixators requires a large incision in the back and dissection of the paraspinal muscles, which is a highly invasive procedure. If the internal fixators must be removed, a second major invasive procedure is required. Moreover, patients undergoing an internal fixation procedure require a lengthy rehabilitation, including reconditioning of the muscles.

The use of external fixators requires the patient to carry a fixation assembly on the surface of the back, which is difficult from a physical and psychological point of view for a majority of patients. Moreover, the rehabilitation of paraplegic patients with external fixators has proven to be difficult.

In addition, external fixators have portals in the skin which become sites for infection.

There is thus a need in the art for skeletal fixation that can be performed with minimal injury to the muscular ligamentous structures.

There is also a need in the art for a method of skeletal fixation whereby the extraction of the fixators is accomplished with minimal surgical intervention.

There is a further need in the art for a method of skeletal fixation which is acceptable both psychologically and cosmetically, and which minimizes infection.

SUMMARY OF THE INVENTION

The present invention provides a method and an apparatus for percutaneous fixation of vertebrae of a patient. The method comprises posterolaterally entering the back of a patient percutaneously with a plurality of pedicle screws, screwing each pedicle screw into the medullary canal of the pedicles of adjacent thoracic and/or lumbar vertebrae or the pedicles of the L5 and S1 vertebrae, to a position where the proximal ends of the screws lie adjacent the fascia of the patient; inserting first and second pedicle screw linkage means under the skin of the back of the patient and detachably securing the linkage means to the proximal ends of said screws on the same side of the spinous processes of said vertebrae to restrict relative movement between the vertebrae.

As can be seen, the method of the present invention requires only a small incision to enable the surgeon to link the pedicle screws together. The fixators are located internally, thereby avoiding the disadvantages of external fixation. Since the subcutaneous fixators used in the present invention may be removed routinely after a period of rehabilitation, such as from 10 to 12 weeks, future MRI and CT visualization of the spinal canal and the lateral recesses are then possible. In contrast, the permanent implantation of internal fixators prevents the use of MRI and CT visualizations.

A alternate embodiment of the present invention provides for both a straight and an offset adaptor for use when a pedicle screw and the linkage means do not properly align. An additional embodiment of the present invention provides for an offset bone bolt to be used with the straight adaptor as a replacement for a pedicle screw and the offset adaptor. The offset bone bolt may also be used with external and deeply implanted internal fixation methods.

The present invention further provides a kit for percutaneous fixation of vertebrae of a patient, comprising a plurality of pedicle screws and/or offset bolts of different sizes, yet of a size to enable the distal end of each screw or bolt to be screwed into the medullary canal of each pedicle of a vertebra with the proximal end thereof lying adjacent the fascia of a patient. The kit may include a plurality of linkage means proportioned to lie under the skin of the patient and operable to detachably link together the proximal ends of the pedicle screws inserted into the pedicles of the vertebrae.

BRIEF DESCRIPTION OF THE DRAWINGS

The present invention is illustrated in terms of its preferred embodiments in the accompanying drawings in which:

FIG. 1 is a schematic view, partly in section in enlarged scale, of one of the pedicles of a lumbar vertebra into which has been inserted a pedicle screw with a beam member detachably linked to the pedicle screw;

FIGS. 3–8 are elevational views of various instruments used to perform the surgical procedure of the present invention;

FIG. 12 is an elevational view of an alternative embodiment of the present invention;

FIG. 13 is a partial sectional view of the alternative embodiment shown in FIG. 12;

FIG. 14 is an elevational view of a second alternative embodiment of the present invention;

FIG. 17 is an elevational view of a third alternate embodiment of the present invention;

FIG. 18 is a partial sectional view of the alternate embodiment show in FIG. 17;

FIG. 19 is a perspective exploded view of an alternate linkage system;

FIG. 20 is a schematic view illustrating the alternate embodiment of FIG. 17 in use as part of a spinal fixation system.

DETAILED DESCRIPTION OF PREFERRED EMBODIMENT

Figure 2:
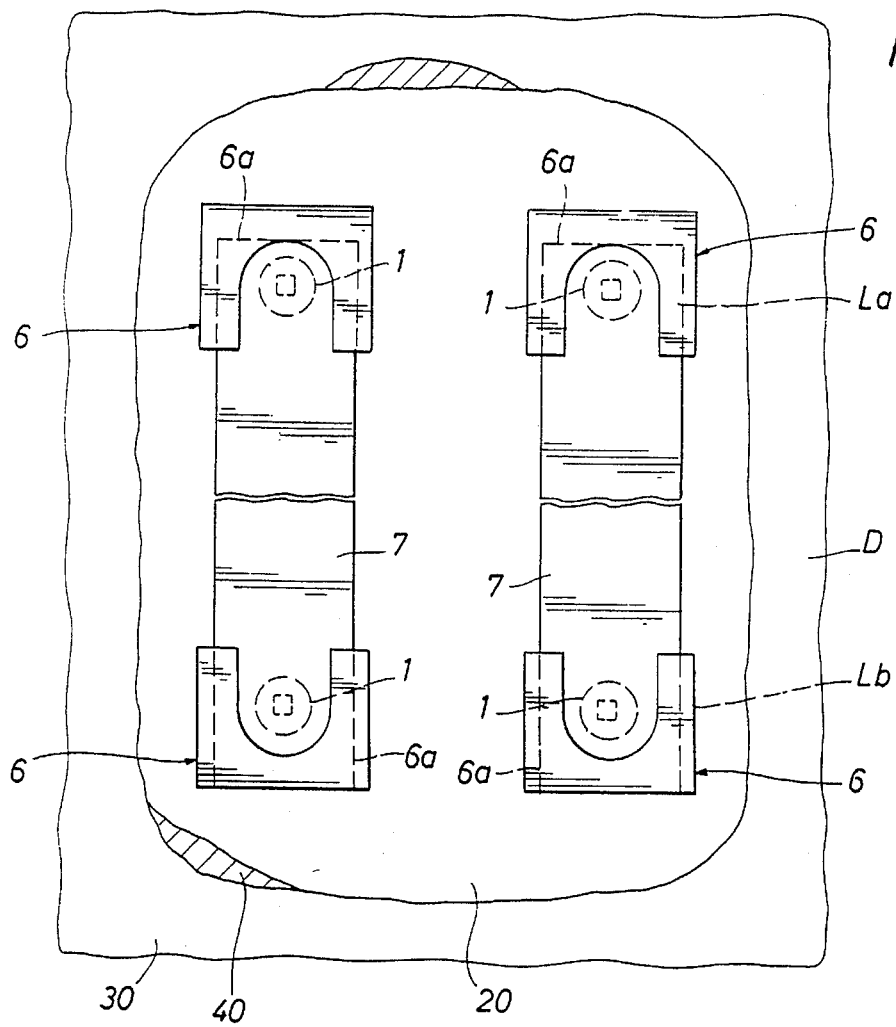
FIG. 2 is a schematic view, in enlarged scale, showing the subcutaneous fixation system of the present invention implanted in a patient.

FIG. 1 schematically shows a pedicle screw 1 inserted into the medullary canal 2 of the pedicle 3 of a lumbar vertebra 4 of a patient. The distal end 1a of the pedicle screw 1 extends into the body 5 of the vertebra 4, while the proximal end 1b lies adjacent to the lumbar fascia 20 (shown in phantom line). Fastened to the proximal end 1b of pedicle screw 1 is an adaptor 6 having a slot 6a therein for receiving a beam member 7, here shown in the form of a plate. FIG. 1 shows the pedicle screw 1 inserted into the pedicle 3 situated to one side of the spinous process (not shown) of the vertebra 4. In the same manner, the pedicle (not shown) lying on the other side of the spinous process is also provided with a pedicle screw and an adaptor. The intervertebral disc to be removed lies between the vertebra 4 shown in FIG. 1 and a lumbar vertebra adjacent thereto (FIG. 2), which is also provided with pedicle screws inserted in the pedicles thereof, adaptors fastened to the proximal ends of the pedicle screws, and a beam member in the same manner as shown in FIG. 1.

FIG. 2 is a schematic view of the assembly of pedicle screws, adaptors and beam members of the invention, as viewed posteriorly with part of the skin 30 and subcutaneous tissue 40 of the patient removed for ease of illustration. Thus, pedicle screws 1 are held in the one pair of the pedicles (not shown) of lumbar vertebra La, while the other pair of pedicle screws 1 is held in the pedicle of vertebra Lb immediately above or below lumbar vertebra La. The intervertebral disc D to be removed is between lumbar vertebra La and Lb as schematically indicated. All of the adaptors 6 are preferably flush against the lumbar fascia 20 as shown in FIG. 1. Pedicle screws 1, adaptors 6, and beam members 7 are all made of biocompatible material, suitably stainless steel.

Figure 5:
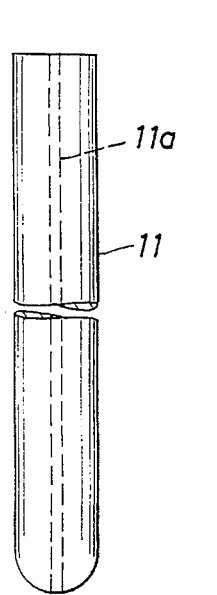
Figure 6:
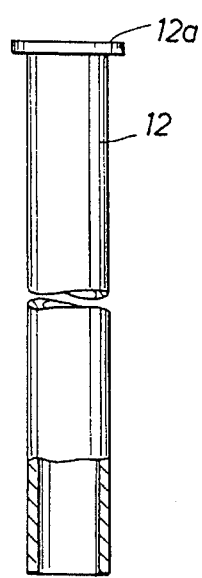

The surgical procedure for percutaneous fixation of lumbar vertebra of the invention may be carried out as follows. The patient is placed prone on a radiolucent table and frame (not shown). The C-arm of a conventional fluoroscope is positioned for anteroposterior visualization of the lumbar vertebrae and the table is tilted away from the C-arm to permit better localization of the pedicles. A cannulated tubular guide 8 (FIG. 3) is maneuvered by hand or by the flexible holder 9 (FIG. 4) having its proximal end 9a secured to the table and carrying at its distal end a ring 9b for holding guide 8. The guide 8 is maneuvered with the holder 9 until the guide 8 is aligned with the longitudinal axis of the pedicle, after which the holder 9 is locked into place. When properly aligned, the guide 8 will appear by fluoroscopy as an opaque circle in the center of the pedicle. A guide wire (not shown), suitably of 2 mm outside diameter, is introduced into the guide 8 and is advanced through the skin of the patient's back, posterolaterally toward the pedicle 3. The guide wire is tapped with a mallet into the cortical bone at the junction of the base of the transverse process 10 (FIG. 1) and the proximal articular process 11. After removal of guide 8, a cannulated obturator 11 (FIG. 5) having a lumen 11a is placed over the guide wire and advanced through the skin of the patient's back to the pedicle 3, followed by placing an access cannula 12 (FIG. 6) over the obturator 11, and advancing the cannula 12 to the pedicle 3.

Figure 7:
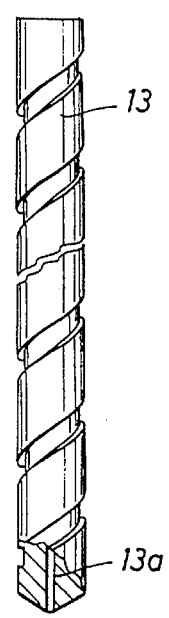
Figure 8:
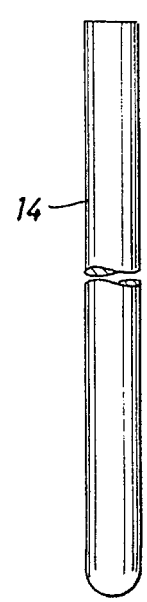

The obturator 11 is then removed, and a cannulated drill 13 having a lumen 13a (FIG. 7) is placed over the guide wire and advanced to the pedicle 3. By manually operating the drill 13, the opening of the cortex of the pedicle is enlarged to form an entrance 3a (FIG. 1) into the medullary canal 3b of the pedicle 3. The cannulated drill 13 is removed and a blunt end pedicle screw probe 14 (FIG. 8) is manually advanced into the medullary canal 3b with a twisting motion, to crush the cancellous bone of the medullary canal 3b thus creating a tunnel or bore 3c (FIG. 1) extending from the pedicle 3 into the vertebral body 5 (FIG. 1). The probe 14 or a blunt end K-wire can be inserted into the bore 3c, the position and length of the probe or K-wire being checked by anteroposterior and lateral fluoroscopy.

If desired by the surgeon, the bore 3c may be tapped to receive the threads 1c of the pedicle screw 1. Alternatively, a self-tapping pedicle screw may be used. Before implanting the pedicle screw 1, the bore 3c may be inspected arthroscopically to make certain that the cortex 3d (FIG. 1) of the pedicle 3 has not been violated; if it has been, the surgeon may abort the procedure.

The length of the pedicle screw 1 to be used may be determined by the use of a K-wire. Thus, the K-wire can be used to measure the depth of bore 3c, and the distance between the bone and the lumbar fascia 20.

Figure 9:
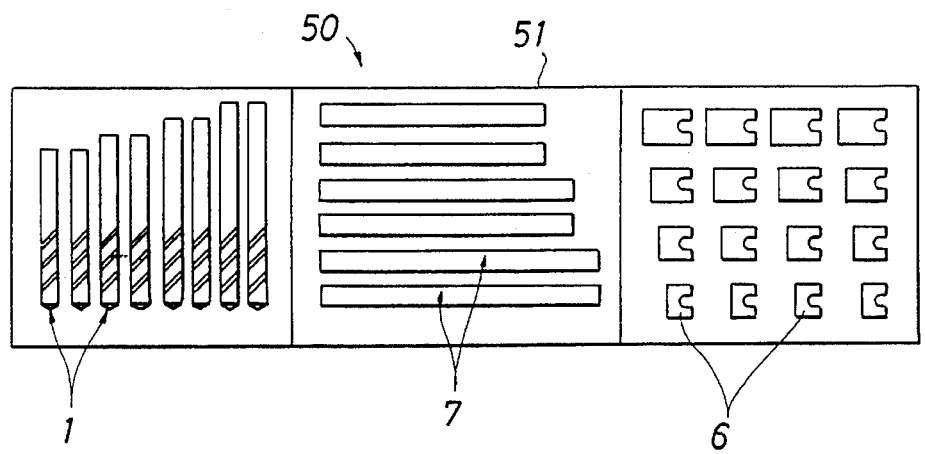
FIG. 9 is a plan view of a kit for carrying out the method of the present invention.

The appropriate pedicle screw 1 is selected from the kit 50 (FIG. 9) containing a plurality of pedicle screws 1, beam members 7 and adaptors 6 in a container 51. The pedicle screws 1 are all of a size to enable the distal end 1a of each screw 1 to be screwed into the medullary canal 3b of the pedicle 3 of a lumber vertebrae with the proximal end 1b thereof lying adjacent the lumbar fascia 20 of a patient, while the beam members 7 are proportioned to lie under the skin 30 of the patient and operate to detachably link together the proximal ends 1b of a pair of pedicle screws 1 (FIG. 2) inserted into the pedicles 3 of the lumbar vertebrae.

Generally, the pedicle screws 1 in kit 50 will be of different lengths and diameters. However, it is contemplated that the kit may contain pedicle screws 1 of different lengths and the same diameters. Moreover, while the beam members 7 may be of different lengths, all are sized to be received in adaptors 6, and since some beam members 7 in the kit 51 may be much longer, they can be cut to length by the surgeon. Adaptors 6 will comprise adaptors having a slot 6a open at one end and closed at the other, such as the upper adaptors 6 as viewed in FIG. 2, while others will have a slot 6a open at both ends, such as the lower adaptors 6 as viewed in FIG. 2.

The pedicle screw 1 selected is placed into the access cannula 12 and thence into the bore 3c. An allen wrench (not shown) may be inserted into the recess 1d (FIG. 1), to drive the pedicle screw 1 into the bore 3c. However, pedicle screw 1 may be provided with any suitable means for engaging a pedicle screw driver, such as a slot in screw 1 and a corresponding blade for the driver.

Figure 10:
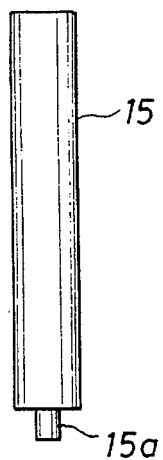
FIG. 10 is an elevational view of a tool used to carry out the method of the present invention.

After pedicle screw 1 is implanted, an adaptor guide 15 (FIG. 10) having an outside diameter smaller than the inside diameter of the tubular body 6b is inserted through the access cannula 12 so that the projection 15a enters recess 1d (FIG. 1), after which the access cannula 12 is removed. An adaptor 6 is slid over the adaptor guide 15 and is screwed in place over the eternal threads on the proximal end 1b of screw 1, to the position shown in FIG. 1. All of the adaptors have an internally threaded tubular body 6b extending from a slotted cap 6c, the slot 6a lying in a plane perpendicular to the tubular body 6b. Adaptor guide 15 may also be used as a driver for the pedicle screws, for example by providing a slot (not shown) in the distal end of guide 15 to receive a cross-bar that serves as a handle.

After the pedicle screws are in place, the disc D is removed by percutaneous total discectomy. See, e.g., U.S. Pat. Nos. 4,573,448, 4,545,374 and 4,678,459. Bone grafts are then packed between the vertebral plates, and the vertebrae are aligned into their desired position by compression, extension and/or angulation using a wrench (not shown) or other tool that securely grasps the proximal ends 1b of the screws and/or the adaptors 6.

When the vertebrae are properly aligned, they are locked in place by inserting the beam members 7 into the adaptors 6 and, in turn, locking the beam members 7 in place. Thus, one end of the beam member 7 is received in an adaptor 6 having a slot 6a open at one end and closed at the other, such as the upper adaptors 6 shown in FIG. 2, while the other end is received in an adaptor 6 having a slot open at both ends, such as the lower adaptors 6 shown in FIG. 2.

To insert the beam member 7 into the adaptors 6, a small incision (not shown), may, if necessary, be made in the patient's back adjacent the adaptor 6 having a slot 6a having two open ends. The beam member 7 is inserted into the subcutaneous tissue 40 via the incision and advanced through adaptors 6 until the distal end of the beam member 7 contacts the closed end of adaptor 6. If necessary, the beam members 7 may be bent to allow the beam member 7 to be received by the adaptors 6. Each beam member 7 is locked in place in adaptors 6 by set screws (not shown) or by crimping the adaptors 6 and the ends of the beam member 7 or by any other suitable detachable locking means. The incision is then closed.

Figure 11:
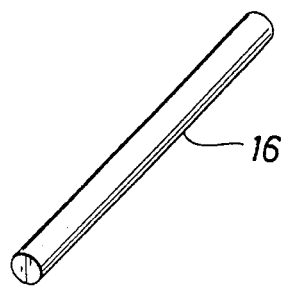
FIG. 11 is a view in perspective of an alternative embodiment of the present invention.

It is presently preferred that the adaptor cap 6 have a low profile, i.e. with a small thickness relative to its length and width. Preferably the cap 6c has a substantially flat top and flat underside as shown, but other configurations may be used as long as the cap 6 is proportioned to lie beneath the skin and/or the lumbar fascia 20. Thus, if the beam members 7 are in the form of rods 16 (FIG. 11), the cap 6 may still be flat but a suitable cylindrical slot (not shown) will be used.

After the pedicle screws are in place, the proximal end 1b of each pedicle screw 1 may not align in a position that allows the beam member 7 to lock in place. Additionally, if the pedicle screw 1 is implanted at an angle into the body 5 of the vertebrae 4 the proximal end 1b of each pedicle screw 1 may touch or be too close together to allow the beam member 7 to lock into place. In these situations an alternative to the adaptor 6 is desirable to allow for easier insertion of the beam member 7. An alternative embodiment of the adaptor 6 is an offset adaptor 60, as shown in FIG. 12. The offset adaptor 60 is an internally threaded tubular body 62 having an offset upper end portion 64 with fine threads 66. FIG. 13 illustrates the internal threading 68 of the tubular body 62, which is designed to engage with the external threads on the proximal end 1b of the pedicle screw 1.

Figure 15:
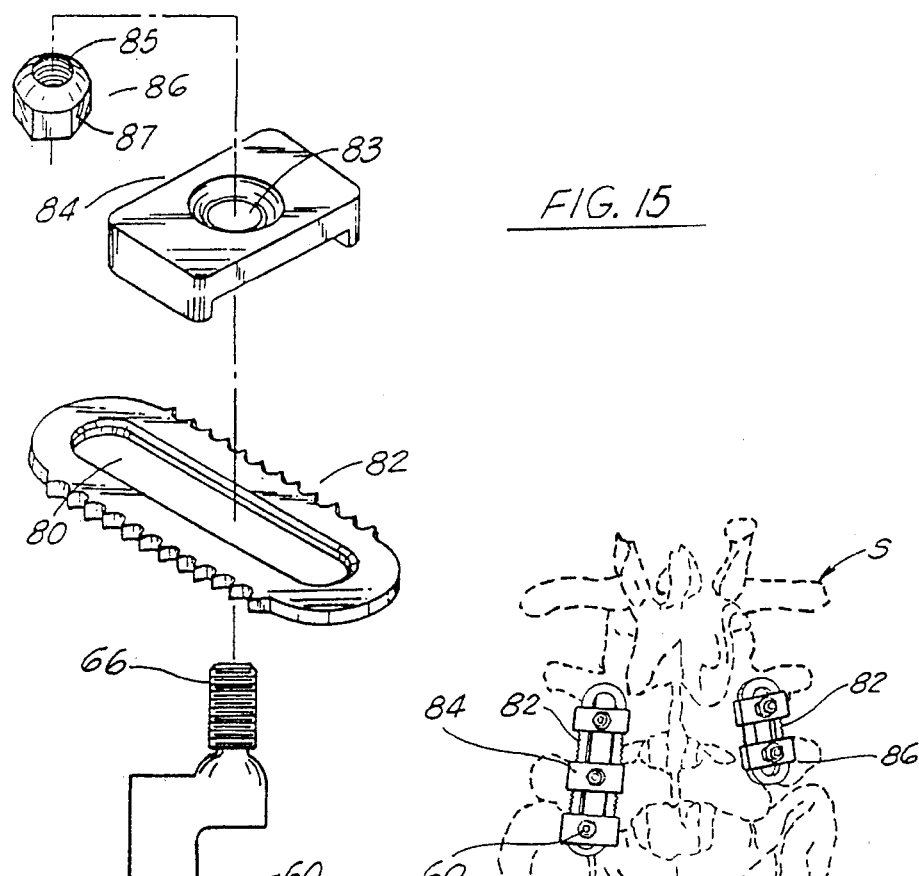
FIG. 15 is a perspective exploded view of an alternative linkage system.

As shown in FIG. 15, the offset adaptor 60 can be used with an alternate linkage system such as a plate 82, a washer 84, and a nut 86 described and shown in U.S. Pat. 5,129,899 which is hereby fully incorporated by reference. The plate 82 has upper and lower surfaces and parallel opposed outer edges with an elongated slot 80 along the central longitudinal axis of the plate 82 with the slot 80 being surrounded by a peripheral portion having the parallel opposed outer edges. The edges have fine adjustment means in the form of teeth or groves that extend between the upper and lower surfaces of the plate 82 for defining various fine adjustment positions of the bone bolt 90 with respect to the plate 82. The washer 84 interfaces with the plate 82 and the bone bolt 90 and has a side portion for engaging the fine adjustment means at the outer edges of the plate 82. The fine adjustment means determine the position of the bone bolt 90 with respect to the plate 82.

The washer 84 has an opening 83 for placement of the proximal end 92 of the bone bolt 90, with the opening 83 having a countersunk portion for receiving a nut. The nut 86 has a longitudinally extending shaped portion 87 that fits the washer 84 at the countersunk opening 83. The nut 86 includes internal threads 85 for cooperation with the fine threads of a bone bolt or adaptor 60 (FIG. 15) or 70 (FIG. 19).

Figure 16:
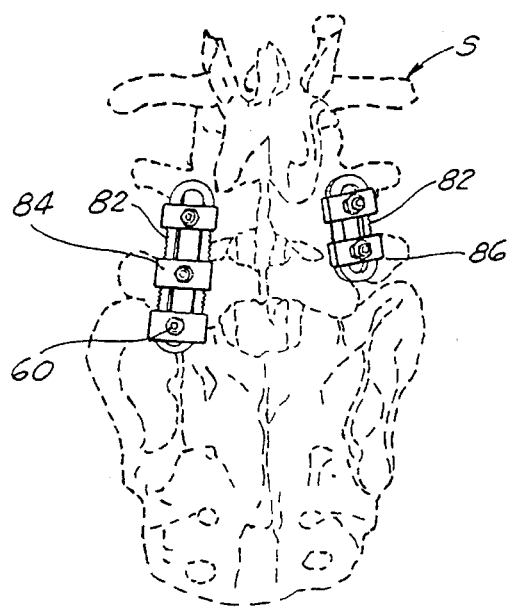
FIG. 16 is a schematic view illustrating an alternate embodiment of the present invention in use as part of a spinal fixation system.

When an alternate linkage system as shown in FIG. 15 is used, the plate 82 is placed over the upwardly projecting screw portion 66 of the offset adaptor 60. The washer 84 is placed over the plate 82 and is secured by the nut 86 that engages the threaded screw portion 66 of the offset adaptor 60. The offset adaptor 60 can be of varying lengths to accommodate the distance between the proximal end 1b of the pedicle screw 1 and the lumbar fascia 20 of the patient. FIG. 16 illustrates a pair of spaced apart plates 82 with the attachment of the offset adaptor 60, the washer 84, and the nut 86 as part of an implanted, overall spinal fixation system.

When the alternate linkage system of FIG. 15 is used, but there is no need to offset the connection between the pedicle screw 1 and the beam member 7, a second alternate embodiment in the form of straight adaptor 70, as shown in FIG. 14, can be used. The straight adaptor 70 has a finely threaded upper end portion 76 and a body 74 that is generally hexagonal in shape. The threaded upper portion 76 engages with the internal threads 85 of the nut 86. The adaptor 70 has an internally threaded portion for engagement with the external threads on the proximal end 1b of the pedicle screw 1. The straight adaptor 70 can be of varying lengths to accommodate the distance between the proximal end 1b of pedicle screw 1 and the lumbar fascia 20 of the patient. Additionally, both adaptor 60 and 70 could be of a sufficient length to be used with an external fixation system. As with the other elements of the system, the adaptors 60 and 70 may be formed of stainless steel or other biocompatable materials.

An alternate fixator to the pedicle screw 1 may be used where, instead of the pedicle screw 1 and the offset adaptor 60, an offset bone bolt 90 and the straight adaptor 70 is used. As shown in FIG. 17, the offset bone bolt 90 has a proximal or upper end portion 92, a middle portion 94 and a distal or lower end portion 96. The middle portion 94 is axially offset from the distal portion 96 and has a load bearing surface 91 for engagement with a linkage system as that illustrated in FIG. 19. The upper end portion 92 of the offset bone bolt 90 has fine threads 93 designed to engage with the internally threaded portion of the adaptor 70 as shown in FIG. 19. The lower end portion 96 has threads 95 typical of those found on bone screws. As shown in FIG. 18, the upper end portion 92 has a recess 98 to accommodate an allen wrench (not shown) or other suitable driver used to implant the offset bone bolt 90 into the pedicle 3 as shown in FIG. 1.

Figure 21:
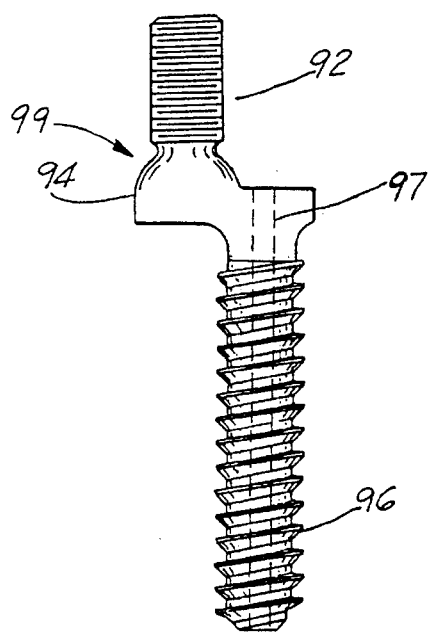
FIG. 21 is a partial sectional view of a forth alternate embodiment of the present invention.

An alternate embodiment of the offset bone bolt 90 is shown in FIG. 21, where an offset bone bolt 99 has a middle portion 94 with a greater offset and the distal portion 96 is cannulated with an aperture 97 extending along the longitudinal axis of the distal portion 96 for allowing a guide wire to extend therethrough. The method of using cannulated bolts or screws with a guide wire is generally described in U.S. Pat. No. 4,790,297.

When an alternate linkage system as shown in FIG. 19 is used, the straight adaptor 70 is placed over the upper end portion 96 of the offset bone bolt 90. The plate 82 is placed over the upwardly projecting portion 76 of the adaptor 70.

The washer 84 is placed over the plate 82 and is secured by the nut 86 that engages the threaded screw portion 76 of the adaptor 70.

Additionally, the offset bone bolt 90 could be of a length sufficient to be used with an external fixation system or of a length appropriate for a deeply implanted fixation system where the fixation system is adjacent to the vertebrae. If desired, the offset bone bolt 90 may be used with a deeply implanted internal fixation system and a linkage system of the type illustrated in FIG. 19. With a linkage system of this type the plate 82 is placed directly over the upwardly projecting portion 92 of the offset bone bolt 90 so that the portion 92 extends through the slot 80 of the plate 82. The undersurface of the plate 82 rests on the load bearing surface 91 of the middle portion 94 of the bone bolt 90. The washer 84 is placed over the plate 82 in such a manner that the proximal portion 92 of the bone bolt 90 extends through the washer opening 83 and is secured by the nut 86 that engages the threaded upper portion 93 of the offset bone bolt 90. As with other elements of the system, the offset bone bolt 90, the plate 82, washer 84 and nut 86 may be formed of stainless steel or other biocompatable materials. FIG. 20 illustrates a pair of spaced apart plates 82 with the attachment of the straight adaptor 70, the washer 84, and the nut 86 as part of an implanted, overall spinal fixation system.

While the drawings show for convenience the fixation of only two vertebrae, it is to be understood that more than two vertebrae may be fixed. For example, when two intervertebral discs are to be removed, say between vertebrae L1, L2 and L3, pedicle screws 1 will be implanted in the pedicles of the three vertebrae. The pedicle screws rising from the L1 or L3 vertebra will carry an adaptor 6 having a slot closed at one end, while the other pedicle screws will carry an adaptor 6 having a slot open at both ends. A longer beam member 7 is then slid through the adaptors 6 and locked into place as described above. Alternately, when more than two vertebrae are fixed the offset adaptor 60 or the straight adaptor 70 may be used in place of the adaptor 6 as seen in FIG. 16. In any of the above procedures the offset bone bolt 90 and 99 and the adaptor 6 or 70 may be used in place of the pedicle screw 1 and the adaptor 6, 60 or 70. Moreover, the surgeon may elect to fix three vertebrae even if only one disc is to be removed.

While the present invention has been illustrated in the accompanying drawings in terms of the fixation of adjacent lumbar vertebrae, it is to be understood that the same procedures are followed for the fixation of adjacent thoracic vertebrae, of adjacent thoracic and lumbar vertebrae and of the L5 and S1 vertebrae. In each case, the procedure is effected percutaneously as described above. That is, the center of each pedicle to be implanted with a pedicle screw or offset bone bolt is located fluoroscopically, the pedicle screws or offset bone bolts are implanted percutaneously as described above and the proximal ends of the pedicle screws or offset bone bolts are linked together beneath the skin at or preferably flush with the muscle fascia as described above. If considered desirable by the surgeon, the beam members and/or the pedicle screws or offset bone bolts may be cross-linked together, such as by the use of 1.5 mm crosswires.

Moreover, while the kit 50 is illustrated as containing the screws, beam members and adaptors 6, the same or auxiliary kits may be provided with adaptors 60, adaptors 70 and/or offset bone bolts 90 and 99 and the instruments used to carry out the surgical procedure, such as the instruments shown in FIGS. 3–8 and 10.

What is claimed is:

1. A bone bolt for internal fixation of bones through the use of a spinal fixation system comprising:
    a) a lower threaded shank portion generally cylindrical in shape having bone threads configured to be surgically implanted into a patient's bone, said lower portion having a central longitudinal axis;
    b) a middle non-threaded portion monolithic with said lower threaded shank portion having a load transfer surface that includes an offset portion radially extending from the lower portion, the offset portion allowing for adjustability in the alignment of the implanted bone bolt in relation to other component parts of a spinal fixation system;
    c) an upper threaded shank portion generally cylindrical in shape monolithic with the middle portion and having a second longitudinal axis spaced laterally away from the first longitudinal axis at the load transfer surface; and
    d) the upper shank portion having cooperating means configured to cooperate with a clamping means and means for engagement with a driver means.

2. The bone bolt according to claim 1, wherein an aperture extends along the central longitudinal axis of the lower portion for cooperating with a guide wire.

3. The bone bolt according to claim 1, further including a bone plate member with fine adjustment means, engagement means interfacing the plate and the bone bolt, and locking means for cooperating with the proximal end portion of the bone bolt and locking the engagement means and plate on the bone bolt.

4. A bone bolt for internal fixation of bones through the use of a spinal fixation system comprising:
    a) an monolithic bolt member that comprises:
        i) a distal threaded shank portion having bone screw threads thereon and configured to be surgically implanted into a patient's bone, said distal shank portion having a first longitudinal axis;
        ii) the threaded shank portion being monolithically connected to a middle non-threaded portion having a load transfer surface that includes a radially extending offset portion axially offset from the distal shank portion, said offset portion allowing for adjustability in the alignment of the implanted bone bolt in relation to other component parts of a spinal fixation system, said middle portion having an inner end that is monolithic with distal shank portion;
        iii) a proximal threaded shank portion that is monolithic with the middle portion and having a second longitudinal axis spaced away from the first longitudinal axis at the load transfer surface; and
    b) wherein the proximal threaded shank includes cooperating means configured to cooperate with a clamping means and means for engagement with a driver means.

5. The bone bolt according to claim 1, wherein the cooperating means comprises threads for threadably receiving a nut.

6. The bone bolt according to claim 1, wherein the means for engagement comprises a hexagonal opening for cooperating with an allen wrench.

7. The bone bolt according to claim 1, wherein an aperture extends along the longitudinal axis of the distal end for cooperating with a guide wire.

* * * * *